United States Patent
Mruzek et al.

[11] Patent Number: 6,134,301
[45] Date of Patent: Oct. 17, 2000

[54] COLLIMATOR AND DETECTOR FOR COMPUTED TOMOGRAPHY SYSTEMS

[75] Inventors: Michael Thomas Mruzek, Clinton, Mich.; David M. Hoffman, New Berlin, Wis.

[73] Assignee: General Electric Company, Milwaukee, Wis.

[21] Appl. No.: 09/102,459

[22] Filed: Jun. 22, 1998

Related U.S. Application Data

[63] Continuation of application No. 08/773,083, Dec. 26, 1996, Pat. No. 5,799,057.

[51] Int. Cl.[7] .......................................................... G21K 1/02
[52] U.S. Cl. ........................................... 378/147; 378/207
[58] Field of Search ........................... 378/145, 147–152, 378/154, 155, 183, 185, 186, 207, 19

[56] References Cited

U.S. PATENT DOCUMENTS

| | | | |
|---|---|---|---|
| 259,574 | 6/1882 | Murdock . | |
| 3,060,941 | 10/1962 | Harloff . | |
| 3,595,248 | 7/1971 | Wright | 132/125 |
| 4,429,227 | 1/1984 | DiBianca et al. | 250/370.09 |
| 4,671,303 | 6/1987 | Saferstein et al. | 132/152 |
| 4,905,717 | 3/1990 | Taylor et al. | 132/148 |
| 5,357,553 | 10/1994 | Ferlic et al. | 378/154 |
| 5,799,057 | 8/1998 | Hoffman et al. | 378/147 |

*Primary Examiner*—David P. Porta
*Attorney, Agent, or Firm*—Armstrong Teasdale; Christian G. Cabou; Phyllis Y. Price

[57] ABSTRACT

The present invention, in one form, is a scatter collimator for a computed tomography system including an x-ray source. The scatter collimator is positioned between a detector array and an object to be imaged. The scatter collimator includes a housing, a plurality of attenuating blades and a plurality of attenuating wires. The blades and wires are mounted to the housing, and oriented substantially perpendicular to each other. Particularly, the blades and wires form a two-dimensional shielding grid. The blades also are oriented so that they are radially and focally aligned with the x-ray source. A detector element of the detector array is secured to the housing so that the blades and wires are between the detector element and the x-ray source. The detector element, in one form, includes a scintillation element which is coated with a light-retaining material.

13 Claims, 8 Drawing Sheets

COLLIMATOR AND DETECTOR FOR COMPUTED TOMOGRAPHY SYSTEMS

This application is a continuation of 08/773,083 filed Dec. 26, 1996, now U.S. Pat. No. 5,799,057.

FIELD OF THE INVENTION

This invention relates generally to computed tomography (CT) imaging and more particularly, to collimators and detectors for use in such systems.

BACKGROUND OF THE INVENTION

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile of the object.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two dimensional slice taken through the object.

One method for reconstructing an image from a set of projection data is referred to in the art as the filtered backprojection technique. This process converts the attenuation measurements from a scan into integers called "CT numbers" or "Hounsfield units", which are used to control the brightness of a corresponding pixel on a cathode ray tube display.

Detector elements are configured to perform optimally when impinged by x-rays travelling a straight path from the x-ray source to the detector elements. Particularly, detector elements typically include scintillation crystals which generate light events when impinged by an x-ray beam. These light events are output from each detector element and directed to photoelectrically responsive materials in order to produce an electrical signal representative of the attenuated beam radiation received at the detector element. Typically, the light events are output to photomultipliers or photodiodes which produce individual analog outputs. Detector elements thus output a strong signal in response to impact by a straight path x-ray beam.

X-rays often scatter when passing through the object being imaged. Particularly, the object often causes some, but not all, x-rays to deviate from the straight path between the x-ray source and the detector. Therefore, detector elements are often impinged by x-ray beams at varying angles.

System performance is degraded when detector elements are impinged by these scattered x-rays. When a detector element is subjected to multiple x-rays at varying angles, the scintillation crystal generates multiple light events. The light events corresponding to the scattered x-rays generate noise in the scintillation crystal output, and thus cause artifacts in the resulting image of the object.

To reduce the effects of scattered x-rays, scatter collimators are often disposed between the object of interest and the detector array. Such collimators are constructed of x-ray absorbent material and positioned so that scattered x-rays are substantially absorbed before impinging upon the detector array. One known scatter collimator is described, for example, in U.S. Pat. No. 5,293,417, assigned to the present assignee. It is important for a scatter collimator to be properly aligned with both the x-ray source and the detector elements so that substantially only straight path x-rays impinge on the detector elements. It is also important that a scatter collimator shield radiation damage sensitive detector elements from x-rays at certain locations, such as the detector element edges.

Known collimators are complicated and cumbersome to construct. In addition, it is difficult to satisfactorily align known collimators with the x-ray source and the detector elements to both absorb scattered x-rays and shield sensitive portions of the detector elements.

Even when a scatter collimator is sufficiently aligned and positioned, detector elements may still generate artifacts. Particularly, detector elements are known to exhibit output gain loss after being subjected to accumulated exposure to x-ray dosage. The extent of output gain loss is directly related to the accuracy and usefulness of the detector element. After exhibiting excessive output gain loss, the detector element must be replaced. Replacing individual detector elements, as well as entire detector arrays, is a time consuming and cumbersome process.

To reduce output gain loss, and thus extend the operational life of detector elements, detector arrays typically include reflectors. Particularly, detectors typically include detector elements forming either one-dimensional or two-dimensional arrays of scintillation crystals having interstitial reflectors. As explained above, when impinged by an x-ray beam, the scintillation crystals produce light events. The reflectors are used to prevent the light within each crystal from escaping the crystal, i.e., to eliminate output gain loss. The interstitial reflectors typically are constructed of foils, coatings or other cast-in-place reflective materials. However, the reflective materials used for the reflectors typically include organic materials which exhibit radiation damage effects over time. Such radiation damage reduces reflector reflectivity, which results in output gain loss. Accordingly, it is desirable to shield the reflectors with the scatter collimator.

It would be desirable to provide a scatter collimator that is not complicated and cumbersome to construct, and that effectively absorbs scattered x-rays and substantially prevents such x-rays from impinging the detector array. It also would be desirable to further reduce detector element output gain loss without significantly increasing the costs of detector elements and detector arrays.

SUMMARY OF THE INVENTION

These and other objects may be attained by a system which, in one embodiment, includes an x-ray source, a scatter collimator and a detector array having a plurality of reflective scintillators. Particularly, and in accordance with one embodiment of the present invention, the scatter collimator includes a housing, and a plurality of substantially parallel attenuating blades and a plurality of substantially parallel attenuating wires are located in the housing.

The attenuating blades, and thus the openings between adjacent attenuating blades, are oriented substantially on a radial line emanating from the x-ray source, i.e., each blade and opening is focally aligned. The blades also are radially aligned with the x-ray source, i.e, each blade is equidistant from the x-ray source. Accordingly, scattered x-rays, i.e., x-rays diverted from radial lines, are attenuated by the blades. The attenuating wires, however, are oriented substantially perpendicular to the blades. The wires and blades thus form a two-dimensional shielding grid for attenuating scattered x-rays and shielding the detector array.

The detector array includes a plurality of detector elements, and is configured to attach to the housing. The detector elements, in one embodiment, include scintillation elements, or scintillators, which are coated with a light-retaining material. Particularly, the scintillators are coated with a dielectric coating to contain light events generated in the scintillators within the scintillators.

The above-described system provides an uncomplicated scatter collimator. In addition, the scatter collimator is believed to effectively absorb scattered x-rays. The coated scintillators are believed to reduce detector element output gain loss without significantly increasing the costs of detector elements and detector arrays.

DETAILED DESCRIPTION OF THE DRAWINGS

Figure 1:
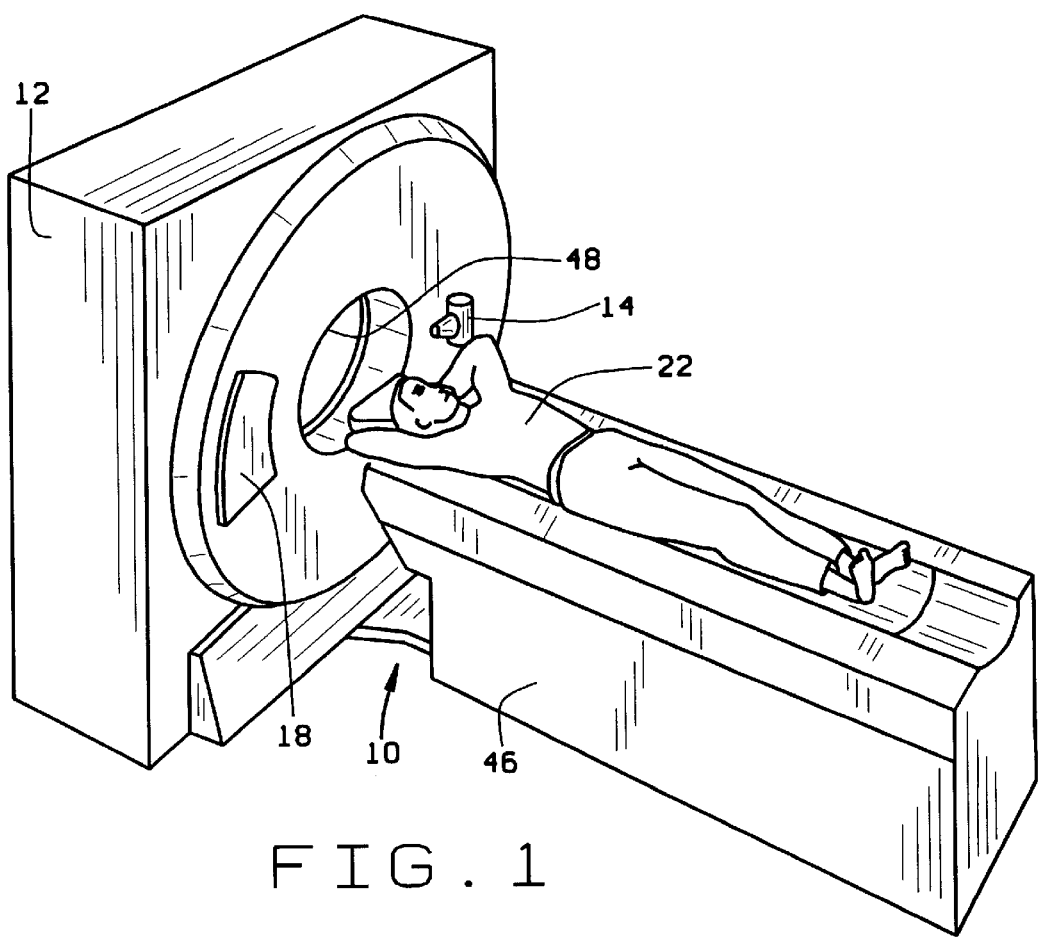
FIG. 1 is a pictorial view of a CT imaging system.
Figure 2:
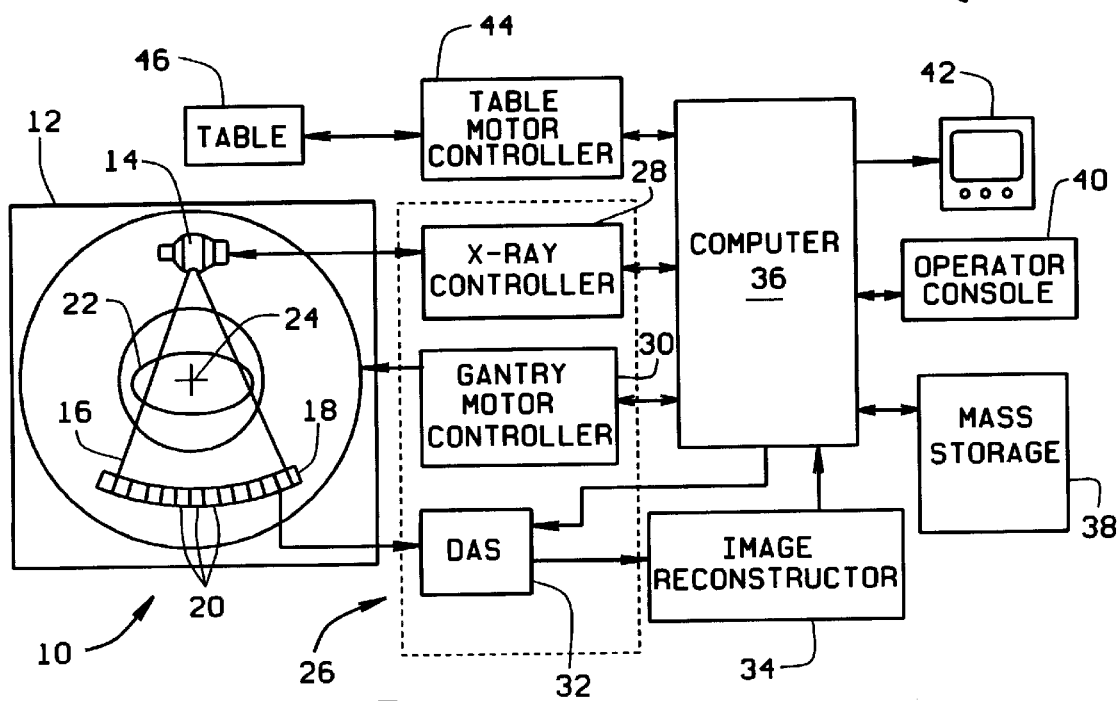
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. X-ray beam is collimated to lie within in an X-Y plane of a Cartesian coordinate system and generally referred to as an "imaging plane". Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
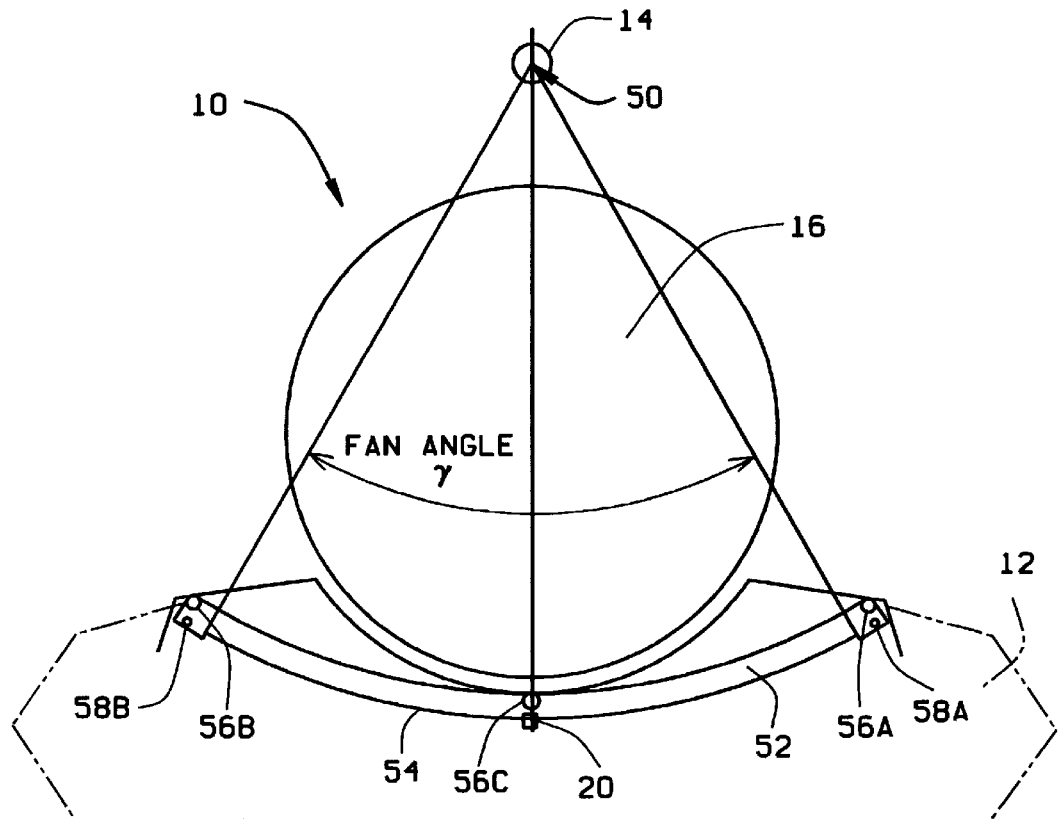
FIG. 3 is a partial pictorial view of the system illustrated in FIG. 1.

FIG. 3 is a partial pictorial view of CT system 10 illustrated in FIG. 1. As shown, x-ray beam 16 emanates from a focal spot 50 of x-ray source 14, and projects a fan of x-rays towards detector elements 20 (only one detector element 20 is shown in FIG. 3) at a far angle γ. CT system 10 is shown as further including a scatter collimator 52, which is positioned between focal spot 50 and detector elements 20. Scatter collimator 52 is curved so that an outer face 54 of scatter collimator 52 is radially spaced from focal spot 52, i.e., all portions of outer face 54 are substantially equidistant from focal spot 50. Detector elements 20 are mounted to scatter collimator 52 so that detector elements 20 similarly are each equidistant from focal spot 50. Scatter collimator 52 is adjustably mounted to gantry 12 with gantry mounts 56A, 56B, and 56C and dowel pins 58A and 58B so that scatter collimator 52 may move relative to focal spot 50.

Figure 4:
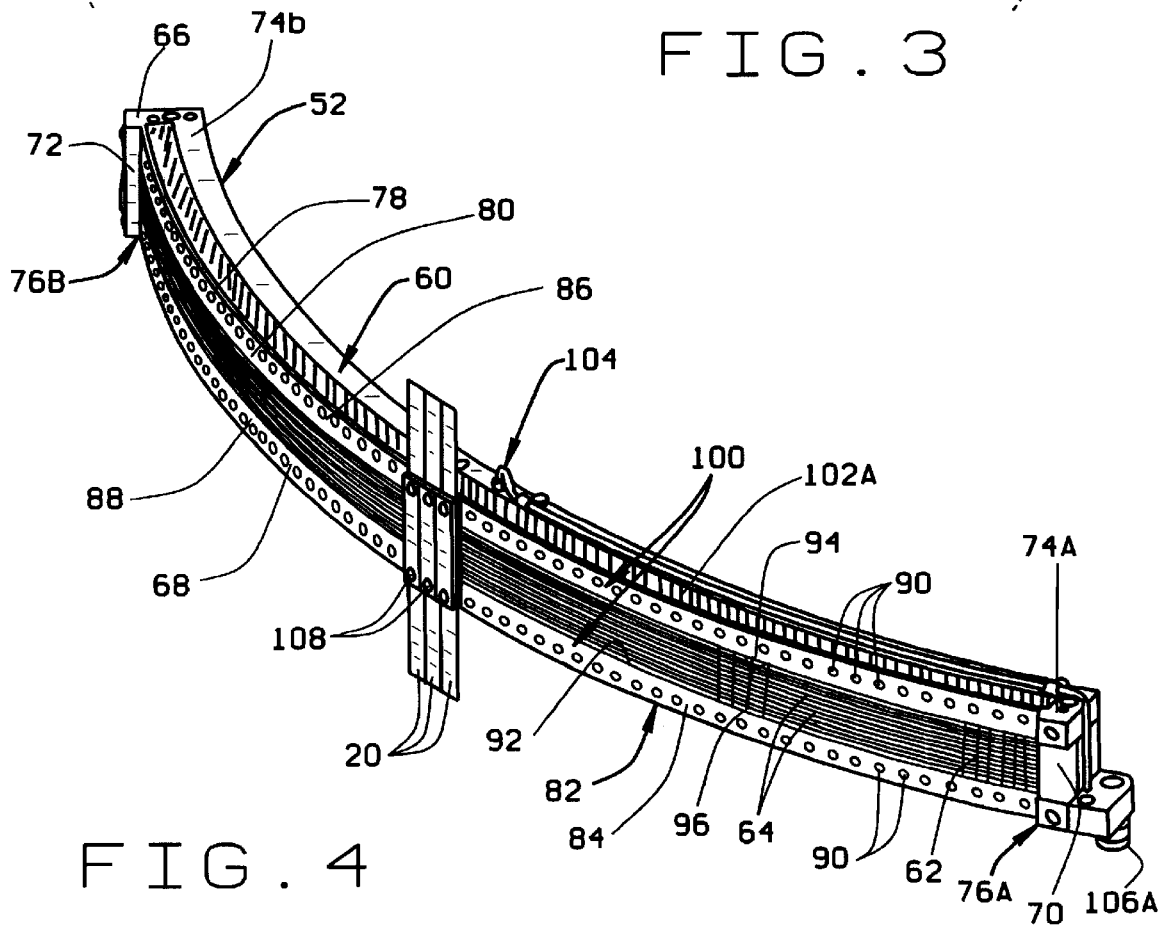
FIG. 4 is a perspective view of a scatter collimator in accordance with one embodiment of the present invention.

Referring to FIG. 4, and in accordance with one embodiment of the present invention, scatter collimator 52 includes a housing 60, a plurality of attenuating blades 62, and a plurality of attenuating wires 64. Housing 60 includes a top rail 66, a bottom rail 68, a first end block 70 and a second end block 72. Each rail 66 and 68 includes first ends 74A and 76A and second ends 74B and 76B, respectively. Top rail 66 further includes a first surface 78 oriented substantially perpendicular to a second surface 80. Similarly, bottom rail 68 includes a first surface 82 oriented substantially perpendicular to a second surface 84. First surfaces 78 and 82 form outer peripheries 86 and 88 of respective rails 66 and 68, and include detector element mounting openings 90, e.g., tapped holes, therein. Outer peripheries 86 and 88 are flush, and form outer face 54 of collimator 52.

Top rail 66 and bottom rail 68 are connected by first end block 70 and second end block 72. Particularly, first ends 74A and 76A of rails 66 and 68 are connected to first end block 70, and second ends 74B and 76B of rails 66 and 68 are connected to second end block 72. Top rail 66 and bottom rail 68 thus extend between blocks 70 and 72 so that there is a blade opening 92 between rails 66 and 68 and end blocks 70 and 72. In addition, rails 66 and 68 are mounted to blocks 70 and 72 so that each detector element mounting opening 90 in rail 66 has a corresponding detector element mounting opening 90 in rail 68. Specifically, rails 66 and 68 are mounted so that lines between corresponding detector element mounting openings 90 are substantially perpendicular to rails 66 and 68. Detector elements 20 (only three detector elements 20 are shown in FIG. 4) are secured to housing 60 via detector element mounting openings 90.

Attenuating blades 62 are constructed of x-ray attenuating material, and are mounted to housing 60 so that blades 62 are between detector elements 20 and focal spot 50. Particularly, attenuating blades 62 are positioned within blade opening 92 of housing 60 and mounted to top and bottom rails 66 and 68. Each attenuating blade 62 is shaped generally rectangularly, and has a first end 94 and a second end 96. First end 94 of each blade 62 is mounted to top rail 66 and second end 94 of each blade 62 is mounted to bottom rail 68 so that each blade 62 extends generally perpendicularly between rails 66 and 68. Blades 62 are aligned within housing 60 so that apertures (not shown) are formed between adjacent blades 62. Each blade 62 also is aligned to be substantially on a radial line emanating from focal spot 50, i.e., blades 62 are "focally aligned". Accordingly, the apertures between blades 62 are substantially on a radial line, and thus scattered x-rays, i.e., x-rays that have diverted from a radial line, are attenuated by blades 62 and do not impinge on detector elements 20.

Attenuating wires 64 are constructed of x-ray attenuating material and are mounted to housing 60 so that wires 64 are between detector elements 20 and focal spot 50. Particularly, attenuating wires 64 are connected to first end block 70 and second end block 72 so that attenuating wires 64 extend across blade opening 92 generally parallel to top rail 66 and bottom rail 68. Attenuating wires 64 are thus substantially perpendicular to attenuating blades 62. Accordingly, attenuating wires 64 and attenuating blades 62 form a shielding grid for protecting detector elements 20. Attenuating wires 64 each have a substantially rectangular cross-sectional shape.

Scatter collimator 52 further includes detector engagement projections 100, or engagement tabs, which project outwardly from outer peripheries 85 and 88 of respective rails 66 and 68. Particularly, detector engagement projections 100 extend substantially perpendicularly from respective second surfaces 80 and 84 of rails 66 and 68. Detector engagement projections 100 are configured so that each detector engagement projection 100 extending from top rail 66 has a corresponding detector engagement projection 100 extending from rail 68, e.g., each detector engagement projection 100 on top rail 66 is substantially vertically aligned with a corresponding detector engagement projection 100 on bottom rail 68. Specifically, detector engagement projections 100 are aligned so that lines between corresponding detector engagement projections 100 are substantially perpendicular to rails 66 and 68. In addition, detector engagement projections 100 are aligned with corresponding mounting openings 90 so that lines between corresponding mounting openings 90 also extend between corresponding detector engagement projections 100.

Scatter collimator 52 also includes electric heaters 102A and 102B (only heater 102A is shown in FIG. 4), a temperature sensor 104, and detector mounting adjusters 106A, 106B and 106C (only detector mounting adjuster 106A is shown in FIG. 4). Electric heater 102A extends between first end block 70 and second end block 72 and is adjacent top rail 66. Particularly, electric heater 102A is positioned adjacent second surface 80 of top rail 66 so that top rail 66 is between electric heater 102A and attenuating blades 62. Electric heater 102B similarly is positioned adjacent second surface 84 of bottom rail 68 so that bottom rail 68 is between electric heater 102B and attenuating blades 62. Temperature sensor 104 likewise is positioned adjacent second surface 80 of top rail 66 so that top rail 60 is between temperature sensor 104 and attenuating blades 62. Specifically, temperature sensor 104 is threaded and screws into top rail 66 so that temperature sensor 104 is adjacent both second surface 80 of top rail 66 and electric heater 102. Detector mounting adjusters 106A, 106B and 106C depend from first end block 70, second end block 72, and at a portion of housing 60 between end blocks 70 and 72, respectively, and are configured to adjustably mount scatter collimator 52 to gantry 12.

Scatter collimator 52 is configured to be secured to detector elements 20. Particularly, detector elements 20 are secured to housing 60 so that in operation, scatter collimator 52 is between detector elements 20 and focal spot 50 and so that detector elements 20 are equidistant from focal spot 50. More specifically, detector elements 20 are connected to top and bottom rails 66 and 68 so that detector elements 20 extend generally perpendicularly to rails 66 and 68. As shown in FIG. 4, detector elements 20 are inserted onto adjacent corresponding detector engagement projections 100 and connected to rails 66 and 68 with, for example, detector element mounting screws 108 which are inserted through detector element mounting openings 90. Particularly, detector elements 20 include notches (not shown) which are sized to receive detector engagement projections 100 therein.

Figure 5:
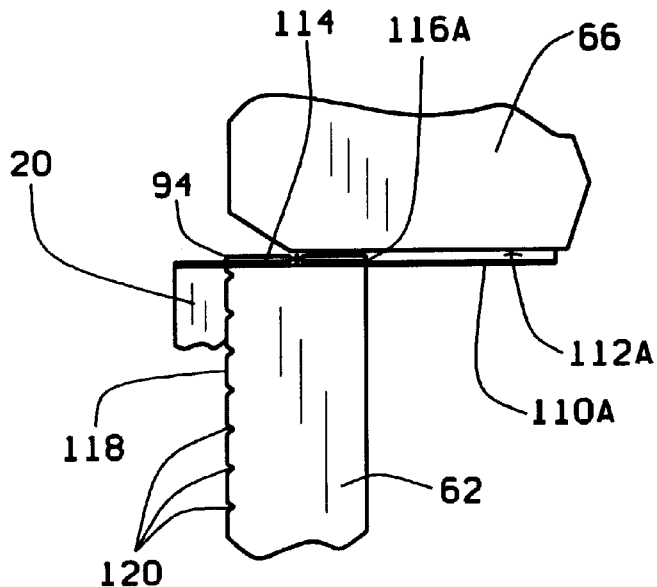
FIG. 5 is a partial side view of the scatter collimator shown in FIG. 4.
Figure 6:
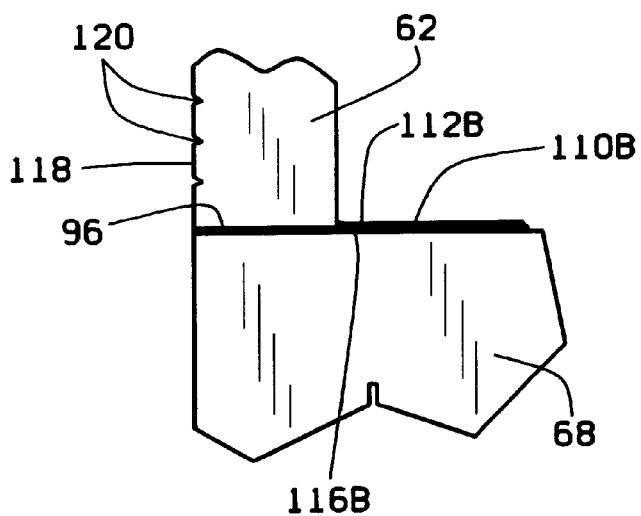
FIG. 6 is a partial side view of the scatter collimator shown in FIG. 4.

FIG. 5 is partial side view of top rail 66, a detector element 20 and an attenuating blade 62, and FIG. 6 is a partial side view of bottom rail 68 and attenuating blade 62. Referring specifically to FIGS. 5 and 6, scatter collimator 52 further includes two blade positioning combs 110A and 110B and two molybdenum stopping elements 112A and 112B. Positioning combs 110A and 110B each include a plurality of teeth 114 having blade receptacles therebetween (only one tooth 114 is shown in each of FIGS. 5 and 6). The blade receptacles are configured to receive attenuating blades 62 therein.

Positioning comb 110A includes an array of five combs (not shown in FIG. 4). Particularly, the five combs each include a plurality of teeth, and are substantially aligned to form positioning comb 110A. Similarly, positioning comb 110B includes an array of five combs that are substantially aligned to form positioning comb 110B. Of course, positioning combs 110A and 10B may each include an array of more than five combs. Alternatively, positioning combs 110A and 110B may each include an array of less than five combs.

Positioning comb 110A is attached to top rail 66, and positioning comb 110B is attached to bottom rail 68. Positioning combs 110A and 110B are connected to rails 66 and 68 so that teeth 114 of respective combs 110A and 110B extend generally perpendicular to second surfaces 80 and 84 of rails 66 and 68. Particularly, positioning combs 110A and 110B are oriented so that when first end 94 of attenuating blade 62 is inserted into a blade receptacle of comb 110A and second end 96 of same blade 62 is inserted into a blade receptacle of comb 110B, blade 62 extends generally perpendicularly between rails 66 and 68.

Stopping elements 112A and 112B include outer surfaces 116A and 116B, respectively, and also are connected to top rail 66 and bottom rail 68, respectively. Particularly, stopping elements 112A and 112B are connected to rails 66 and 68 so that outer surfaces 116A and 116B are radially distant from, or radially aligned with, focal spot 50, i.e., each portion of outer surfaces 116A and 116B is equidistant from focal spot 50. Stopping elements 112A and 112B are positioned adjacent respective positioning combs 110A and 110B to control the extent to which blades 62 may be inserted into the blade receptacles of combs 110A and 110B. More specifically, outer surfaces 116A and 116B of stopping elements 112A and 112B form "walls" between adjacent teeth 114 of respective combs 110A and 112B.

Still referring to FIGS. 5 and 6, attenuation blade 62 is shown as including an outer surface 118 having a plurality of notches 120 therein. Notches 120 are configured to receive portions of attenuating wire 64 therein, so that attenuating wires 64 may be stabilized across the detector elements 20. Notches 120 may, for example, be machined into blades 62.

Figure 7:
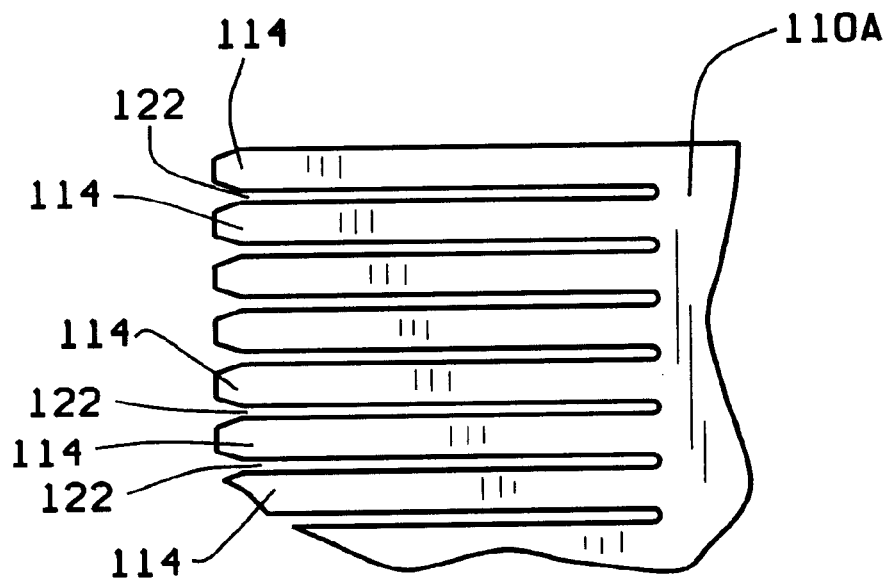
FIG. 7 is a top view of a positioning comb in accordance with one embodiment of the present invention.

FIG. 7 illustrates positioning comb 110A as including teeth 114 having blade receptacles 122 therebetween. As described above, blade receptacles 122 are configured to receive blades 62 therein. In addition, while not shown, positioning comb 110B has similar teeth 114 and blade receptacles 122.

To assemble scatter collimator 52, top and bottom rails 66 and 68 are connected to first end block 70 and second end block 72 as described above. Positioning combs 110A and 10B and stopping elements 112A and 112B are connected to top rail 66 and bottom rail 68, respectively. Particularly, positioning combs 110A and 110B are secured to top rail 66 and bottom rail 68, respectively, so that positioning comb teeth 114 project substantially equidistantly from outer peripheries 86 and 88 of respective rails 66 and 68. Combs 110A and 110B also are positioned so that positioning comb teeth 114 extend substantially along on radial line emanating from focal spot 50, i.e., teeth 114 are "focally aligned" with focal spot 50. Stopping elements 112A and 112B are secured to positioning combs 110A and 110B so that stopping element outer surfaces 116A and 116B are radially distant from focal spot 50.

Figure 8A:
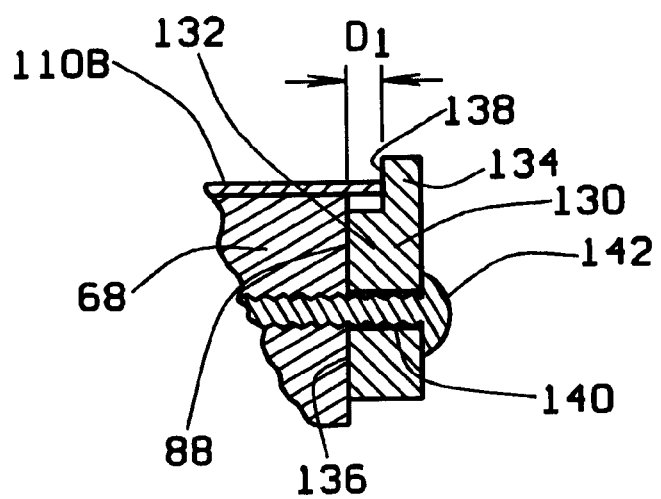
FIGS. 8a and 8b illustrate a stop block for securing positioning combs to the top and bottom rails of a collimator housing in accordance with one embodiment of the present invention.
Figure 8B:
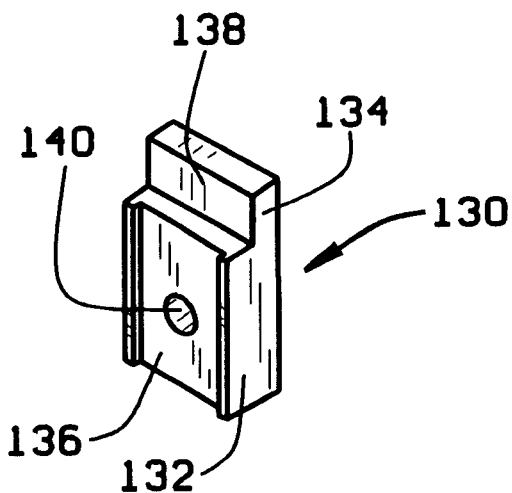

FIGS. 8a and 8b illustrate a stop block 130 for securing positioning combs 110A and 110B to top rail 66 and bottom rail 68, respectively (only comb 110B and bottom rail 68 are visible in FIGS. 8a and 8b). Stop block 130 includes a rail portion 132 and a comb portion 134. Rail portion 132 includes a rail surface 136 which is configured to abut bottom rail 68. Comb portion 134 includes a comb surface 138 which is spaced at a distance $D_1$ from rail surface 136.

To secure comb 110B to bottom rail 68, stop block 130 is positioned adjacent bottom rail 68 so that outer periphery 88 of bottom rail 68 abuts rail surface 136. Accordingly, rail surface 136 has a curvature substantially the same as the curvature of bottom rail outer periphery 88. Particularly, in one embodiment, stop block 130 includes an opening 140 extending therethrough, and a screw 142 is inserted through opening 140 to secure stop block 130 to bottom rail 68. After positioning stop block 130, comb 110B is secured to bottom rail 68 so that teeth 114 of comb 110B extend between bottom rail 68 and comb surface 138 of stop block 130. Particularly, teeth 114 abut comb surface 138 so that teeth 114 extend substantially equidistantly from outer periphery 88 of bottom rail 68. Accordingly, comb teeth 114 are radially aligned with focal spot 50 of x-ray source 14. Comb 110A is similarly secured to top rail 66.

Figure 9A:
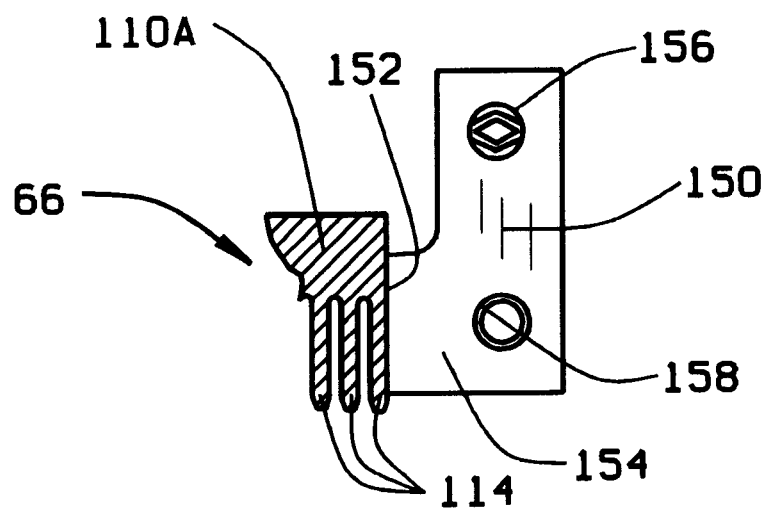
FIGS. 9a and 9b illustrate a comb angle block for focally aligning the teeth of a positioning comb on the top and bottom rails of a collimator housing in accordance with one embodiment of the present invention.
Figure 9B:
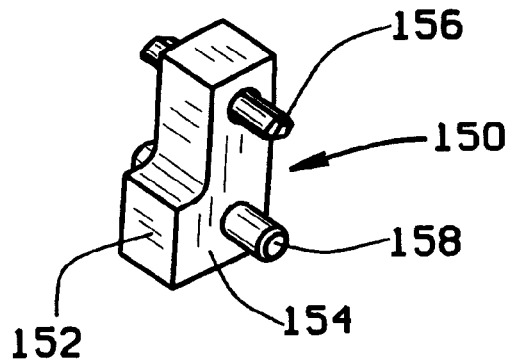

FIGS. 9a and 9b illustrate a comb angle block 150 for focally aligning teeth 114 of positioning combs 110A and 110B on top rail 66 and bottom rail 68, respectively (only comb 110A and top rail 66 are visible in FIGS. 9a and 9b). Comb angle block 150 is substantially "L" shaped and includes a comb surface 152 at the base 154 thereof. Comb angle block 150 also includes a diamond pin 156 and a round pin 158, each pin extending through comb angle block 150.

Prior to securing combs 110A and 110B to rails 66 and 68, respectively, comb angle block 150 is positioned adjacent top rail 66 as shown. Positioning comb 110A is then so that positioned comb 110A abuts comb surface 152. Particularly, as shown, positioning comb 110A is positioned so that an outer tooth 114 of positioning comb 110A is substantially flush with comb surface 152 of comb angle block 150. More specifically, a first comb of positioning comb 110A is positioned with comb angle block 150. The other combs of positioning comb 110A are positioned using the first comb. Similarly, comb angle block 150 is positioned adjacent bottom rail 68 and positioning comb 110B is positioned so that an outer tooth 114 of positioning comb 110B is substantially flush with comb surface 152. Particularly, a first comb of positioning comb 110A is positioned with comb angle block 150, and the other combs are positioned using the first comb. Accordingly, comb teeth 114 are focally aligned with focal spot 50 of x-ray source and comb teeth 114 are of comb 110A are substantially aligned with comb teeth 114 of comb 110B. Therefore, blade receptacles 122 are substantially aligned and configured to retain blades 62 substantially perpendicular to rails 66 and 68.

Figure 10A:
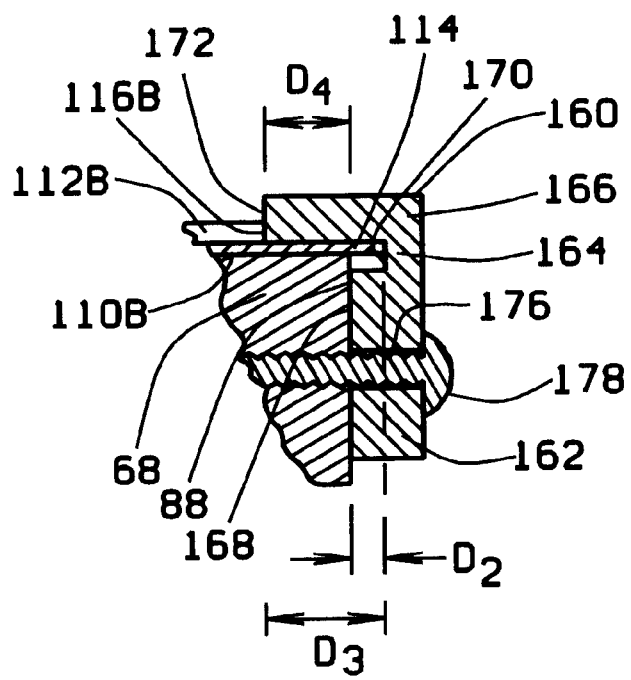
FIGS. 10a and 10b illustrate a finger block for connecting stopping elements to the top and bottom rails of a collimator housing in accordance with one embodiment of the present invention.
Figure 10B:
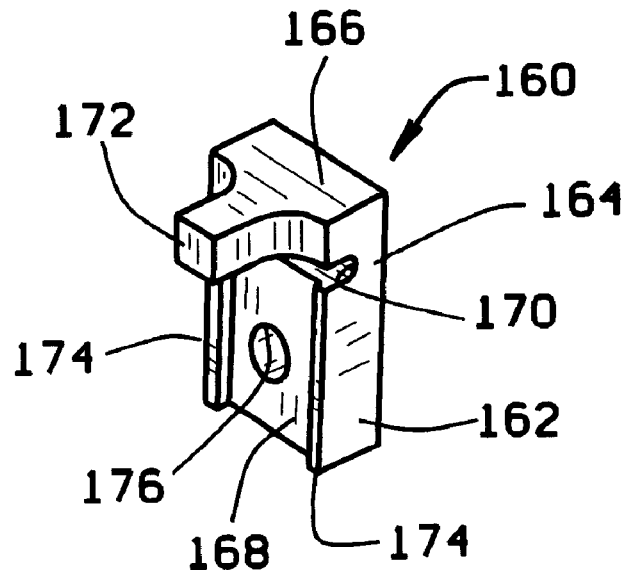

FIGS. 10a and 10b illustrate a finger block 160 for connecting stopping elements 112A and 112B to top rail 66 and bottom rail 68, respectively (only stopping element 112B and bottom rail 68 are visible in FIGS. 10a and 10b). Finger block 160 includes a rail portion 162, a comb portion 164, and a stopping element portion 166. Rail portion 162 includes a rail surface 168 which is configured to abut bottom rail 68. Comb portion 164 includes a comb surface 170 which is spaced at a distance $D_2$ from rail surface 168. Stopping element portion 166 includes a stopping element surface 172 which is spaced at a distance $D_3$ from comb surface 170.

To secure stopping element 112B to bottom rail 68, finger block 160 is positioned adjacent bottom rail 68 so that outer periphery 88 of bottom rail 68 abuts rail surface 168 and so that teeth 114 of comb 110B extend between rail surface 168 and comb surface 170. Specifically, rail surface 168 includes two elevated ridges 174, and finger block 160 is positioned so that outer periphery 88 of bottom rail 68 abuts elevated ridges 174. As shown, teeth 114 of comb 110B do not abut comb surface 170. In one embodiment, finger block 160 includes an opening 176 extending therethrough, and a screw 178 is inserted through opening 176 to secure finger block 160 to bottom rail 68. After positioning finger block 160, and as shown, stopping element portion 166 extends a distance $D_4$ over bottom rail 68 and comb 110B. Stopping element 112B is secured to bottom rail 68 so that outer surface 116B of stopping element 112B abuts stopping element surface 172 of stopping element portion 166 at distance $D_4$ from outer periphery 88 of bottom rail 68. Accordingly, outer surface 116B of stopping element 112B is radially aligned with focal spot 50 of x-ray source 14. Stopping element 112A is similarly secured to top rail 66.

Attenuating blades 62 are then inserted into blade receptacles 122 of combs 110A and 110B so that blades 62 are substantially parallel and abut outer surfaces 116A and 116B of stopping elements 112A and 112B. Accordingly, blades 62 are radially aligned with, i.e., equidistant from, focal spot 50. Blades 62, as described above, also are angularly positioned so that they are focally aligned with focal spot 50. Blades 62 are then bonded to combs 110A and 110B. Attenuating wires 64 are then positioned in blade notches 126 and secured to first end block 70 and second end block 74 as described above. Particularly, wires 64 are bonded to end blocks 72 and 74. Scatter collimator 52 is then mounted to gantry 12 via detector mounting adjusters 106A, 106B and 106C.

Figure 11:
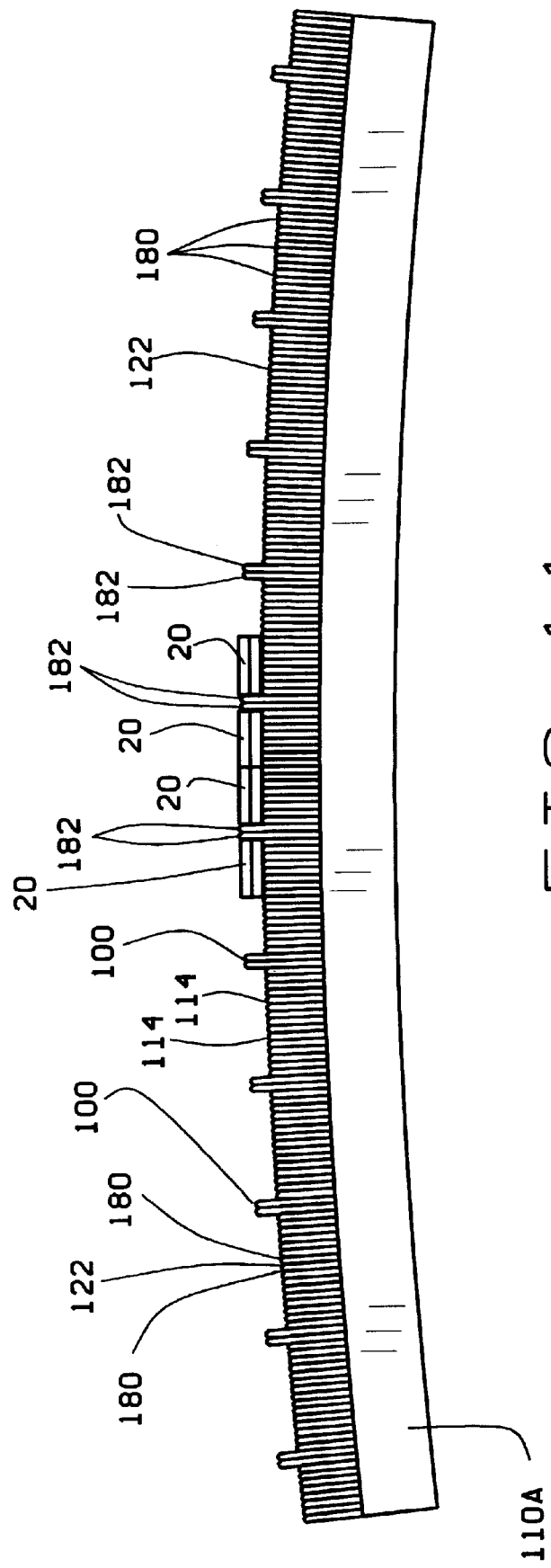
FIG. 11 is an expanded top view of the positioning comb and comb teeth shown in FIG. 7.

FIG. 11 is an expanded top view of positioning comb 110A and comb teeth 114. Particularly, teeth 114 include blade grasping teeth 180 and detector element engaging teeth 182. Blade grasping teeth 180, as described above, have blade receiving receptacles 122 therebetween, and are configured to receive attenuating blades 62 within blade receiving receptacles 122. Detector element engaging teeth 182, however, form detector element projection tabs 100 which are configured to couple to detector elements 20.

Figure 12:
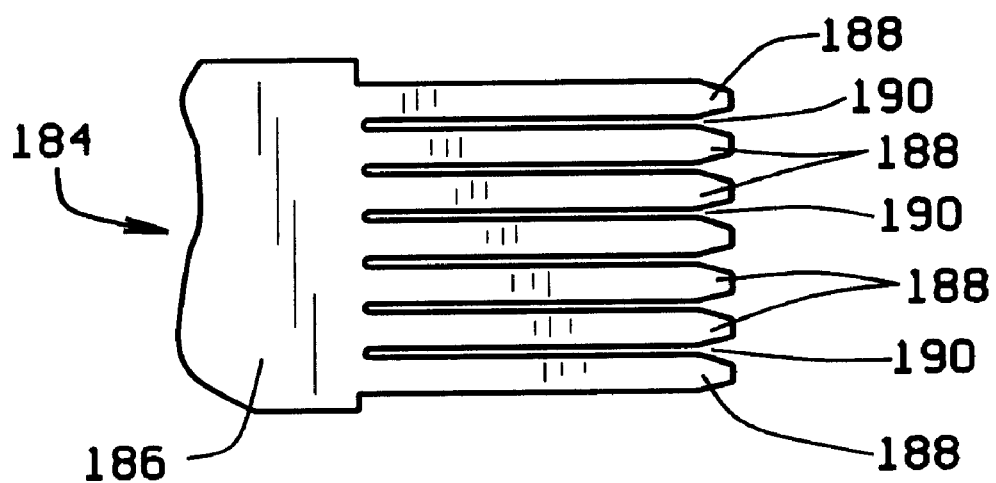
FIG. 12 is a partial top view of a blade combing tool in accordance with one embodiment of the present invention.

To facilitate proper blade alignment, i.e., to verify that blades 62 are substantially parallel, and referring to FIG. 12, a blade combing tool 184 may be used. Blade combing tool includes a handle 186 and a plurality of teeth 188 extending from handle 186. Teeth 188 are substantially parallel and include cavities 190 therebetween. Cavities 190 are configured to receive blades 62 therein, while teeth 188 are configured to be inserted between adjacent blades 62. Teeth 188 are substantially the same thickness. To use combing tool 184, teeth 188 are inserted between adjacent blades 62 so that blades 62 slide into cavities 190. Combing tool 184 then brushes blades 62 to verify that adjacent blades 62 are equidistant from each other at all portions of such blades 62, i.e., blades 62 are substantially parallel. Accordingly, combing tool 184 facilitates accurate blade alignment and thus substantially eliminates improper blade deflection.

The above-described scatter collimator provides for substantially precise alignment with both the focal spot and the detector elements. Also, the scatter collimator is not complex, and is more simple to construct than known scatter collimators. In addition, the scatter collimator sufficiently shields the detector elements from undesirable scattered x-rays and other radiation. Accordingly, the scatter collimator is believed to provide improved system performance as compared to known collimators.

To further improve system performance, detector elements 20 include scintillation elements that are coated with a light-retaining material, i.e., a material which maintains light within each respective scintillation element. Detector elements 20 could be configured so that the scintillation elements form an array having interstitial reflectors. Accordingly, the coating of light-maintaining material is positioned between each scintillation element and an interstitial reflector. The light-retaining coating thus substantially contains light events generated in the scintillation elements within such scintillation elements, and reduces the amount of light exiting the scintillation elements and reflecting off of the interstitial reflectors. Therefore, it is believed that detector element overall gain loss is reduced.

The above-described embodiments substantially prevent scattered x-rays and unwanted radiation from impinging detector elements 20. In addition, the coated scintillation elements reduce the extent of interstitial reflector reflectivity loss and, thus, detector element gain loss. However, such embodiments were illustrated only for exemplary purposes. Additional embodiments are, of course, possible.

The light-retaining coating applied to the scintillation elements may be, for example, a loaded epoxy. Alternatively, of course, the light-retaining coating may be a thin metal coating, i.e., a semi-transparent coating, a low index coating, a dielectric coating or a dielectric stack coating. The light-retaining coating may also be an intermediary in-organic coating layer. Of course, other light-retaining coatings also may be used.

Furthermore, attenuating blades 62 may be constructed of Tungsten. However, attenuating blades 62 may be constructed of other attenuating material. Similarly, attenuating wires 64 may be constructed of Tungsten or some other attenuating material. In addition, while stopping elements 112A and 112B described herein are constructed of molybdenum, stopping elements 112A and 112B may be constructed of other material.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, although the CT system described herein is a "third generation" system, many other systems, such as "fourth generation" systems may be used. In addition, the positioning combs described herein each included an array of five combs. Alternatively, each positioning comb may include either fewer or more than five combs, e.g., three, four, or six combs. Accordingly, the spirit and scope of the invention are to be limited only by the terms of the appended claims.

What is claimed is:

1. A combing tool and collimator for use in connection with a computed tomography system, said collimator including a plurality of attenuating blades, each of said blades extending substantially parallel to an adjacent one of said blades, said combing tool comprising a handle and a plurality of substantially parallel teeth having cavities therebetween extending from said handle, said tool configured to verify alignment of said collimator blades.

2. A combing tool and collimator in accordance with claim 1 wherein said teeth are configured to be inserted between adjacent said attenuating blades.

3. A combing tool and collimator in accordance with claim 1 wherein each of said cavities is configured to receive at least one said attenuating blade.

4. A combing tool and collimator in accordance with claim 1 wherein said teeth each have a substantially different thickness.

5. A combing tool and collimator for use in connection with a computed tomography system, said collimator including a plurality of attenuating blades, each of said blades extending substantially parallel to an adjacent one of said blades, and said combing tool comprising means for verifying alignment of said collimator blades.

6. A combing tool and collimator for use in connection with a computed tomography system, said collimator including a plurality of attenuating blades, each of said blades extending substantially parallel to an adjacent one of said blades, and said combing tool comprising a plurality of substantially parallel teeth having cavities therebetween and configured to verify alignment of said collimator blades.

7. A combing tool and collimator in accordance with claim 6 wherein said teeth are configured to be inserted between adjacent said attenuating blades.

8. A combing tool and collimator in accordance with claim 6 wherein each of said cavities is configured to receive at least one said attenuating blade.

9. A combing tool and collimator in accordance with claim 6 wherein said teeth have a substantially similar thickness.

10. A method for ensuring that attenuating blades of a collimator are substantially parallel using a combing tool having a plurality of substantially parallel teeth having cavities therebetween, said method comprising the step of inserting the combing tool teeth between adjacent attenuating blades.

11. A method in accordance with claim 10 wherein each of the cavities is configured to receive at least one attenuating blade.

12. A method in accordance with claim 11 further comprising the step of brushing the blades.

13. A method in accordance with claim 10 further comprising the step of brushing the blades.

\* \* \* \* \*